United States Patent
Maeda

(10) Patent No.: US 10,126,279 B2
(45) Date of Patent: Nov. 13, 2018

(54) MASS ANALYSIS DATA PROCESSING APPARATUS AND MASS ANALYSIS DATA PROCESSING METHOD

(71) Applicant: SHIMADZU CORPORATION, Kyoto-shi, Kyoto (JP)

(72) Inventor: Kengo Maeda, Takarazuka (JP)

(73) Assignee: SHIMADZU CORPORATION, Kyoto-shi, Kyoto (JP)

(*) Notice: Subject to any disclaimer, the term of this patent is extended or adjusted under 35 U.S.C. 154(b) by 271 days.

(21) Appl. No.: 14/812,013

(22) Filed: Jul. 29, 2015

(65) Prior Publication Data

US 2016/0033458 A1    Feb. 4, 2016

(30) Foreign Application Priority Data

Jul. 30, 2014 (JP) .................................. 2014-154532

(51) Int. Cl.
G01N 30/72    (2006.01)
G01N 30/86    (2006.01)

(52) U.S. Cl.
CPC ......... *G01N 30/86* (2013.01); *G01N 30/7233* (2013.01)

(58) Field of Classification Search
CPC ..... G01N 30/86; G01N 30/7233; G01J 49/26; G01J 49/005; H01J 49/005; H01J 49/26
See application file for complete search history.

(56) References Cited

U.S. PATENT DOCUMENTS

| 8,884,218 B2 * | 11/2014 | Yamaguchi | H01J 49/004 250/281 |
| 2006/0145070 A1 * | 7/2006 | Hondo | G01N 30/7233 250/288 |

(Continued)

FOREIGN PATENT DOCUMENTS

| JP | 2004-251830 A | 9/2004 | |
| JP | 2004251830 | * 9/2004 | ............ G01N 30/86 |
| JP | 2010-019655 A | 1/2010 | |

OTHER PUBLICATIONS

Communication dated Jun. 27, 2017 from the Japanese Patent Office in counterpart Application No. 2014-154532.

*Primary Examiner* — Bryan Bui
(74) *Attorney, Agent, or Firm* — Sughrue Mion, PLLC

(57) ABSTRACT

To enhance the efficiency in the operation of checking a plurality of mass spectra acquired by measuring MS" (n is an integer equal to or more than two) of a sample containing an unidentified component under a plurality of measurement conditions. A mass analysis data processing apparatus for processing data constituting a plurality of mass spectra acquired by performing MS" (n is an integer equal to or more than two) measurement of an unidentified component contained in a sample under a plurality of different measurement conditions, the apparatus including: a determination condition input unit 43 for allowing an analyst to input a determination condition concerning a maximum intensity value of mass peaks on the mass spectra, in order to select, out of the plurality of mass spectra, a mass spectrum or mass spectra effective for presuming the unidentified component; a determination execution unit 44 for determining whether or not the determination condition is satisfied in each of the plurality of mass spectra; and a selection result presentation unit 45 for selecting a mass spectrum or mass spectra, determined to satisfy the determination condition by the (Continued)

determination execution unit 44, and presenting the mass spectrum or spectra to the analyst.

10 Claims, 6 Drawing Sheets

(56) References Cited

U.S. PATENT DOCUMENTS

| | | | |
|---|---|---|---|
| 2008/0073501 A1* | 3/2008 | Yamaguchi | H01J 49/0036 250/282 |
| 2010/0133428 A1* | 6/2010 | Matsui | H01J 49/0045 250/281 |

* cited by examiner

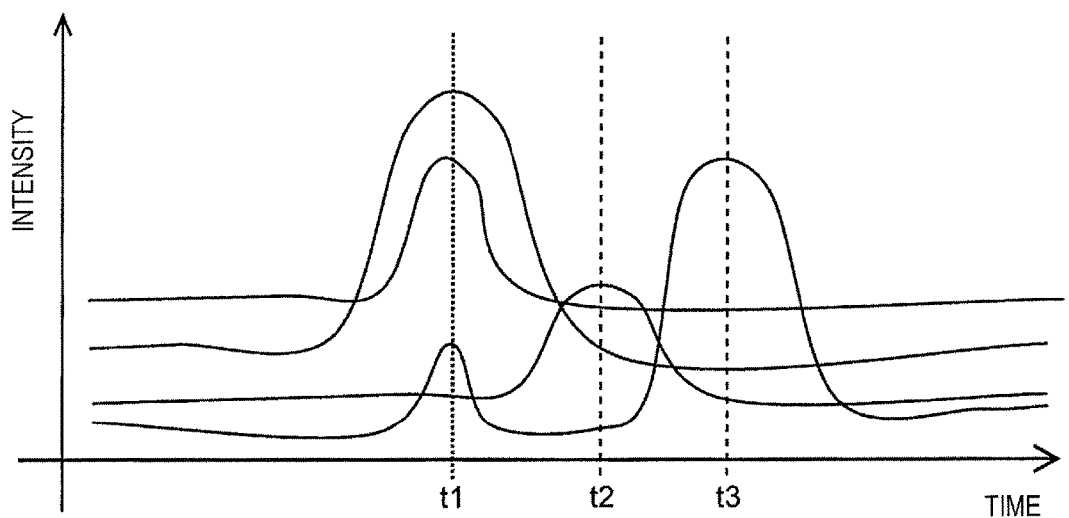

MASS ANALYSIS DATA PROCESSING APPARATUS AND MASS ANALYSIS DATA PROCESSING METHOD

TECHNICAL FIELD

The present invention relates to an apparatus and method for processing a plurality of mass spectrum data acquired by measuring $MS^n$ (n is an integer equal to or more than two) of a sample containing an unidentified component under a plurality of measurement conditions.

BACKGROUND ART

In order to presume an unidentified component contained in a sample (hereinafter referred to as "unidentified component"), scan measurement is widely used, which uses a chromatograph mass spectrometer structured by combining a chromatograph, such as a gas chromatograph (GC) and a liquid chromatograph (LC), with a mass spectrometer (MS). A combined apparatus (LC/MS) of the LC with a mass spectrometer having one mass separation unit is used to perform MS scan measurement, whereas a combined apparatus (LC/MS/MS) of the LC with a mass spectrometer having a collision cell and mass separation units, which are positioned before and after the collision cell, is used to perform MS/MS scan measurement.

In LC/MS scan measurement, ions generated from unidentified components are measured as they are to acquire the mass spectra of the ions. In product ion scan measurement using the LC/MS/MS, ions are generated from unidentified compounds separated in time in a column of the LC. Out of the generated ions, ions having a specific mass-to-charge ratio are selected as a precursor ion in a front-stage mass separation unit, and then the precursor ion is fragmented in the collision cell to generate product ions. The generated product ions are further subjected to scan measurement in a rear-side mass separation unit to acquire the mass spectra of the product ions. Hence, it is possible to obtain more detailed information about the molecular structure of the unidentified component than that in the LC/MS scan measurement. Therefore, the product ion scan measurement with the LC/MS/MS is typically performed in presuming a compound having a complicated molecular structure, such as agricultural chemicals and medicinal substances (see, for example, Patent Literature 1).

When product ion scan measurement is performed with use of the LC/MS/MS to inspect whether the sample contains agricultural chemicals, medicinal substance, or the like, a plurality of compounds, whose mass spectra of product ions are known, are selected as inspection subjects in advance. Then, measurement conditions for each of the plurality of subject compounds are set. The conditions include values of the mass-to-charge ratios of precursor ions that characterize each of the subject compounds. While an unidentified component is being eluted from a column of the LC, product ion scan measurements are executed in sequence under the plurality of measurement conditions to acquire the mass spectra of the subject compounds. When an unidentified component corresponds to one of the subject compounds, a mass spectrum (i.e., the position (mass-to-charge ratio) and the intensity of mass peaks on the mass spectrum) obtained under the measurement condition corresponding to the corresponding subject compound, matches with the mass spectrum representing (the position and the intensity of mass peaks of) the corresponding subject compound. Therefore, it is possible to determine whether or not the unidentified component is one of the subject compounds by confirming matching between the positions and the intensities of mass peaks on the mass spectra, each acquired by measurement performed under the plurality of measurement conditions during elution of the unidentified component, and the positions and the intensities of the mass peaks on the mass spectra of the subject compounds.

In recent years, a database storing the mass spectra of the product ions concerning a large number of compounds is provided. If a matching degree between the positions (mass-to-charge ratios) and the intensities of the mass peaks on the mass spectra of various compounds in the database and the positions and the intensities of the mass peaks on the mass spectra acquired by measurement is calculated by a data processor, an analyst can confirm the result to presume an unidentified component contained in a sample in a relatively simple manner.

However, in the inspection of prohibited substances contained in a sample derived from a living body, for example, not only principal subject compounds (hereinafter referred to as "basic compounds") but also compounds (similar compounds) whose molecular structures are partially altered from those of the basic compounds need to be detected. A series of subject compound groups, including the basic compounds and the compounds similar to the basic compounds, have molecular structures mostly in common. However, since the molecular structures of the similar compounds are partially altered, the mass spectra of their product ions do not match with the mass spectra of the product ions of the basic compounds. Accordingly, the analyst cannot determine the presence of the similar compounds simply by confirming the result of calculating the matching degree with the mass spectra stored in the compound database. Therefore, in the inspection of medicinal substances and the like, the analyst confirms the presence of similar substances by displaying on a display device a plurality of mass spectra acquired by performing MS/MS measurement and comparing the positions and the intensities of mass peaks on each of the mass spectra to find out mass peaks that characterize the subject compound groups.

CITATION LIST

Patent Literature

[Patent Literature 1] JP 2010-19655 A

SUMMARY OF INVENTION

Technical Problem

In recent years, high-speed scan measurement techniques have been improved, so that scan measurement can be performed under a large number of measurement conditions during elution of an unidentified component. This makes it possible to efficiently acquire the mass spectra of product ions under measurement conditions in which the ions that characterize a large number of subject compound groups are set as a precursor ion. However, at the same time, a larger burden is put on the analysts who check a large number of mass spectra.

Although an unidentified component is presumed by checking the mass spectra acquired by performing MS/MS ($=MS^2$) measurement in the above-described case, the same problem arises in the case of checking the mass spectra acquired by performing product ion scan measurement of $MS^3$ or more, or in the case of checking the mass spectra acquired by performing other scan measurement (precursor ion scan measurement and neutral loss scan measurement).

An object of the present invention is to provide a mass analysis data processing apparatus and a mass analysis data processing method, which can enhance the efficiency in the operation of checking a plurality of mass spectra acquired by performing scan measurement of a sample containing an unidentified component under a plurality of measurement conditions.

Solution to Problem

A first form of the present invention made to attain the above object is a mass analysis data processing apparatus for processing data constituting a plurality of mass spectra acquired by performing $MS^n$ (n is an integer equal to or more than two) measurement of an unidentified component contained in a sample under a plurality of different measurement conditions, the apparatus including: a) a determination condition input unit for allowing an analyst to input a determination condition concerning a maximum intensity value of mass peaks on the mass spectra, in order to select, out of the plurality of mass spectra, mass spectra effective for presuming the unidentified component; b) a determination execution unit for determining whether or not the determination condition is satisfied in each of the plurality of mass spectra; and c) a selection result presentation unit for selecting a mass spectrum or mass spectra, determined to satisfy the determination condition by the determination execution unit, and presenting the mass spectrum or spectra to the analyst.

The $MS^n$ measurement includes not only product ion scan measurement, but also precursor ion scan measurement using a mass spectrometer having mass separation units provided before and after a collision cell. In the precursor ion scan measurement, a front-stage quadrupole is used to execute a precursor ion scan, and a rear-stage quadrupole is used to pass the product ions having a specific mass-to-charge ratio. The $MS^n$ measurement also includes neutral loss scan measurement using a mass spectrometer having the same structure, in which a front-stage quadrupole is used to execute a precursor ion scan, and a rear-stage quadrupole executes a production ion scan so as to pass the product ions whose mass-to-charge ratio has a fixed difference from the mass-to-charge ratio of the ions passing the front-stage quadrupole.

As described in the foregoing, in the case of presuming an unidentified component in a sample, a plurality of subject compounds, whose mass spectra are known, are selected in advance. Then, measurement conditions for each of the plurality of compounds are set. The conditions include a value of the mass-to-charge ratio of a precursor ion that characterizes each of the subject compounds. Under the plurality of measurement conditions, $MS^n$ (n is an integer equal to or more than two) measurement is executed in sequence so that the mass spectra of the product ions are acquired. The mass analysis data processing apparatus according to the present invention processes the data constituting such mass spectra of the product ions, for example.

The measurement conditions corresponding to the plurality of subject compounds (or subject compound groups) are so set that product ions peculiar to subject compounds or their similar compounds are detected with high intensity, when scanning measurement is executed. Ideally, a mass peak appears only on the mass spectrum acquired under the measurement condition for a subject compound corresponding to a measured component, and mass peaks do not appear on the mass spectra acquired under the measurement conditions for the subject compounds not corresponding to the measured component. In practice, however, mass peaks may appear on the mass spectra acquired under the measurement conditions for the subject compounds not corresponding to the measured component.

For example, when a component (compound A) eluted from the column of the LC in the LC/MS/MS is positively ionized, univalent molecular ions caused by proton addition are mainly generated. Therefore, in the measurement condition for the subject compound A, a mass-to-charge ratio of the univalent molecular ion as a precursor ion is set. In practice, not only univalent molecular ions, but also adduct ions caused by addition of sodium ions, ammonium ions, and the like, as well as multi-charged ions caused by addition of a plurality of protons, are also generated. When the mass-to-charge ratios of the adduct ions or the multi-charged ions match with (or approximate to) the mass-to-charge ratio of the ion, which is set as a precursor ion of a different subject compound B, a mass peak also appears on the mass spectrum acquired under the measurement condition for the subject compound B However, since the generation efficiency of adduct ions and/or multi-charged ions is generally lower than the generation efficiency of univalent molecular ions, a mass peak intensity on a mass spectrum acquired under the measurement condition for the subject compound B, which is not corresponding to the measured component, is smaller than a mass peak intensity on the mass spectrum acquired under the measurement condition for the subject compound A corresponding to the measured component. Although a noise peak may appear on the mass spectrum, the noise peak intensity is generally smaller than the mass peak intensity on the mass spectrum acquired under the measurement condition for the subject compound A.

More specifically, when a mass peak intensity appearing on the mass spectrum obtained under the measurement condition for the subject compound (or a subject compound group) corresponding to an unidentified component is compared with a mass peak intensity appearing on the mass spectrum obtained under the measurement condition for the subject compound which does not correspond to the unidentified component, the former intensity is generally larger.

In the mass analysis data processing apparatus according to the present invention, based on the determination condition concerning a maximum value of the mass peak intensities on the mass spectra input by the analyst, the mass spectra having only noise peaks and/or the mass spectra which do not correspond to the measured compound are determined to be ineffective in identification of the unidentified component, and only mass spectra effective in presuming the unidentified component are selected and presented to the analyst. Therefore, the analyst does not need to check the mass spectra which do not contribute to the presumption of the unidentified component (i.e., the mass spectra which do not contain mass peaks of significant intensities). As a result, the efficiency in the check operation is enhanced.

For example, the determination condition may be that there is included a mass peak intensity exceeding a certain threshold. This determination condition can adequately be used when the absolute value of a noise peak intensity, which should be excluded in the measurement system, is known, is assumable, or is easily determined based on a measurement result. Specifically, the determination condition can adequately be used when the magnitude of generated noise is generally constant and the generated noise peak intensity is known, such as mechanical noises and electric noises. The determination condition can also adequately be used in the case of excluding a chemical noise which originates from impurity and whose intensity is known (in the case of excluding peaks originating from a mobile phase, peaks originating from a matrix, peaks originating from a reference sample, and the like). In addition, the determination condition can adequately be used when, for example, the analyst can perform scan measurement while confirming mass peak intensities on the mass spectra on the screen or the like of a measuring apparatus. This is because the analyst can determine a threshold value suitable for determining the mass spectra based on the absolute value of the mass peak intensities.

The determination condition may be that there is included a mass peak whose intensity is equal to or larger than a certain percentage of the maximum intensity value, which is the maximum among the mass peak intensities on the plurality of mass spectra. This determination condition can adequately be used when the intensity of a noise peak, which should be excluded in the system of measurement, can relatively be determined as a certain ratio to the mass peak intensity of the subject compound. Specifically, the determination condition can adequately be used in the case of excluding peaks of a chemical noise originating from the impurity (e.g., the impurity difficult to completely dissociate in the pretreatment such as refining of the sample) whose concentration changes in proportion to the concentration of the subject compounds. In addition, the determination condition can adequately be used in the case of, for example, determining a mass spectrum acquired in advance by scan measurement. In this case, since the absolute value of a mass peak intensity is unknown, the determination condition that leads to a relative evaluation of the mass peak intensities to each other, among a plurality of mass spectra, can adequately be used.

The determination condition may further be defined as a ratio between an intensity value of a maximum intensity mass peak in each of the mass spectra and an average value of all the mass peak intensities on each of the mass spectra being equal to or more than a specified value. Also in this case, the determination condition can be input even when the absolute value of the mass peak intensity is unknown as in the above case. The condition is also adequate in the case of selecting mass spectra containing a significant mass peak when the acquired mass spectra contain a large number of noise peaks, because the intensity value of the maximum intensity mass peak on each of the mass spectra is compared with an average value of all the mass peak intensities.

A second form of the present invention made to attain the above object is a mass analysis data processing method for processing data constituting a plurality of mass spectra acquired by performing $MS^n$ (n is an integer equal to or more than two) measurement of an unidentified component contained in a sample under a plurality of different measurement conditions, the method comprising: a) allowing an analyst to input a determination condition concerning a maximum intensity value of mass peaks on the mass spectra, in order to select, out of the plurality of mass spectra, a mass spectrum or mass spectra effective for presuming the unidentified component; b) determining whether or not the determination condition is satisfied in each of the plurality of mass spectra; and c) selecting a mass spectrum or mass spectra, determined to satisfy the determination condition, and presenting the mass spectrum or spectra to the analyst.

Advantageous Effects of Invention

By using the mass analysis data processing apparatus and/or the mass analysis data processing method according to the present invention, it is possible to enhance the efficiency in the operation of an analyst checking a plurality of mass spectra acquired by performing $MS^n$ (n is two or more) measurement for a sample containing an unidentified component under a plurality of measurement conditions.

In the past, an analyst needed to check all of a large number of mass spectra acquired by scan measurement and to determine whether or not each of the mass spectra is effective for presuming an unidentified component. Accordingly, there was a possibility that the analyst might overlook the effective mass spectra in the process of checking a large number of mass spectra. By using the mass analysis data processing apparatus or method according to the present invention, the analyst may check only the mass spectrum or spectra determined to be effective for the presumption of the unidentified component. This makes it possible to reduce the possibility of overlooking the effective mass spectrum or spectra by the analyst.

BRIEF DESCRIPTION OF DRAWINGS

FIG. 3 is a total ion chromatogram illustrating retention time of components in a sample in this embodiment.

FIG. 4 is a determination condition input screen in this embodiment.

DESCRIPTION OF EMBODIMENTS

The embodiment of the mass analysis data processing apparatus and the mass analysis data processing method according to the present invention will be described below with reference to the drawings.

The mass analysis data processing apparatus of this embodiment processes the data constituting mass spectra acquired by product ion scan measurement performed in a chromatograph mass spectrometer (LC/MS/MS). The LC/MS/MS is structured as a combination of a liquid chromatograph and a tandem mass spectrometer including a collision cell and quadrupole mass separation units provided before and after the collision cell.

Figure 1:
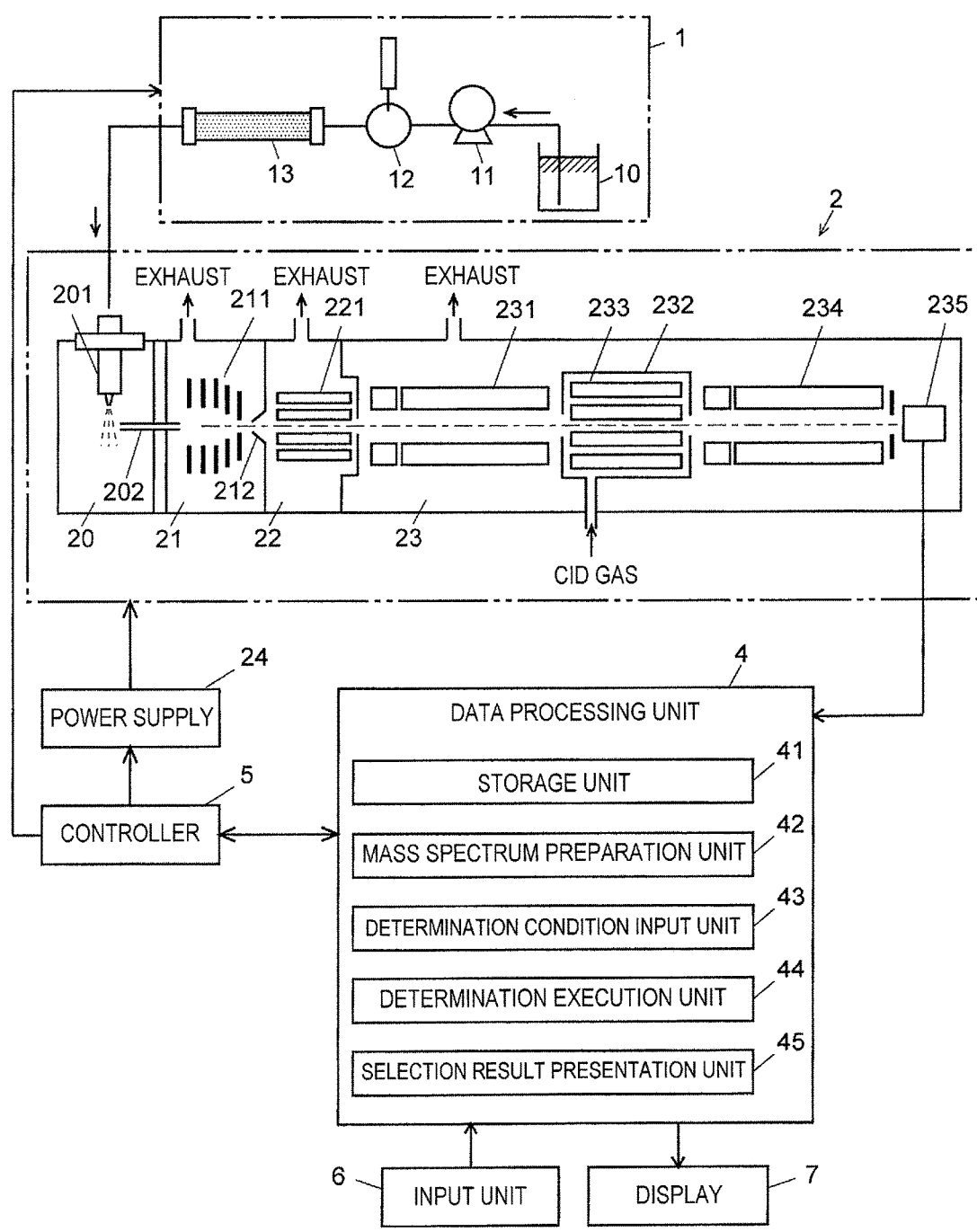
FIG. 1 is a block diagram of principle components of a liquid chromatograph mass spectrometer including a data processing apparatus as one embodiment of the mass analysis data processing apparatus according to the present invention.

FIG. 1 illustrates a block diagram of principle components of the LC/MS/MS including the mass analysis data processing apparatus of this embodiment.

The LC/MS/MS includes a liquid chromatograph unit 1 and a mass analyzing unit 2.

The liquid chromatograph unit 1 includes a mobile phase container 10 for storing a mobile phase, a pump 11 for sucking and supplying the mobile phase at a constant flow, an injector 12 for injecting a sample containing an unidentified component into the mobile phase, and a column 13 for temporally separating components (sample components) in the sample. Each component separated in the column 13 is introduced into the mass analyzing unit 2 in sequence.

The mass spectrometer 2 has the structure of a multiple-stage differential pumping system, including first and second middle vacuum chambers 21 and 22 provided in between an ionization chamber 20 having an approximately atmospheric pressure and a high-vacuum chemical chamber 23 evacuated by a vacuum pump which is not illustrated. In the first and second middle vacuum chambers 21 and 22, a degree of vacuum is gradually increased. The ionization chamber 20 is equipped with an electro-spray ionization probe 201 (ESI probe) that sprays a sample solution while applying charge to the sample solution. The ionization chamber 20 is in communication with the rear-stage first middle vacuum chamber 21 through a heating capillary 202 with a narrow diameter. The first middle vacuum chamber 21 and the second middle vacuum chamber 22 are separated by a skimmer 212 having an apex portion where a small hole is provided. The first middle vacuum chamber 21 and the second middle vacuum chamber 22 are provided with ion guides 211 and 221 for focusing and transporting ions to the rear stage, respectively. The chemical chamber 23 includes a collision cell 232 in which a multipole ion guide (q2) 233 is internally provided. The collision cell 232 is interposed in between a front-stage quadrupole mass filter (Q1) 231 that separates ions in accordance with mass-to-charge ratios and a rear-stage quadrupole mass filter (Q3) 234 that similarly separates ions in accordance with the mass-to-charge ratios. The chemical chamber 23 further includes an ion detector 235.

In the case of MS/MS analysis, a CID gas, such as argon and nitrogen, is supplied to the inside of the collision cell 232 continuously or intermittently, and a voltage whose value is preset as collision energy is applied. The power supply 24 applies predetermined voltages to each of the electro-spray ionization probe 201, the ion guides 211, 221, and 233, the quadrupole mass filters 231 and 234, and the like.

In the mass spectrometer 2, when a mixed liquid of the sample components separated in the column 13 and the mobile phase reaches the ESI probe 201, the eluate is sprayed while receiving charge at the distal end of the probe 201 so that the elute is ionized. Charged droplets formed by spraying are miniaturized while being divided by the action of electrostatic force caused by the applied charge. During this process, a solvent evaporates and ions originating from the sample components are generated. The ions are sent to the first middle vacuum chamber 21 through the heating capillary 202 to be focused by the ion guide 211, and are sent to the second middle vacuum chamber 22 through the hole on the apex portion of the skimmer 212. The ions are then focused by the ion guide 221 and sent to the chemical chamber 23, where the ions are introduced to a space in a major axis direction of the front-stage quadrupole mass filter 231. Ionization may be achieved not only by the electro-spray ionization method but also by an atmospheric pressure chemical ionization method, an atmospheric pressure photoionization method, and the like.

At the time of performing product ion scan measurement, the power supply 24 applies predetermined voltages (voltages obtained by superimposing RF voltage on DC voltage) to each rod electrode of the front-stage quadrupole mass filter 231 and the rear-stage quadrupole mass filter 234. The CID gas is supplied continuously or intermittently to the collision cell 232. Among various ions sent to the front-stage quadrupole mass filter 231, only the ions having a specific mass-to-charge ratio in proportion to the voltage currently applied to each rod electrode of the front-stage quadrupole mass filter 231 pass the filter 231 and are introduced to the collision cell 232 as a precursor ion. Inside the collision cell 232, the precursor ions collide with the CID gas and are dissociated into various kinds of product ions. In the rear-stage quadrupole mass filter 234, a mass scan is performed, and the mass-to-charge ratio of the product ions passing the filter 234 changes continuously. The ions which passed the rear-stage quadrupole mass filter 234 reach the ion detector 235 to be detected. In the ion detector 235, pulse signals the number of which is in proportion to the number of input ions are output to a data processing unit 4 as a detection signal, which is stored in a storage unit 41 as a detection result.

The data processing unit 4 has the storage unit 41. The data processing unit 4 also includes as a functional block, a mass spectrum preparation unit 42, a determination condition input unit 43, a determination execution unit 44, and a selection result presentation unit 45. The mass spectrum preparation unit 42 prepares a total ion chromatogram and mass spectra based on the detection result of the ion detector 235 stored in the storage unit 41, and extracts the position and intensity of each mass peak on the mass spectra. The data processing unit 4 is also configured to suitably transmit and receive signals to/from a controller 5 that controls operation of each unit, such as the pump 11 and the injector 12 of the liquid chromatograph unit 1, and the power supply 24 and a CID gas supply unit (not illustrated) of the mass analyzing unit 2. The data processing unit 4 is physically embodied by a personal computer. When data processing software preinstalled in the computer is executed, the function as the data processing unit 4 can be demonstrated. The data processing unit 4 is connected to an input unit 6 and a display 7.

In this embodiment, the product ion scan measurement with the LC/MS/MS is performed to inspect whether or not a biological sample contains any one of a plurality of types of medicinal substances (hereinafter referred to as "subject compounds"). Product ion measurement conditions are preset for the plurality of subject compounds, respectively. The conditions include a mass-to-charge ratio of a precursor ion that characterizes each of the subject compounds, collision energy for fragmenting the precursor ion, and a mass scan range of the product ion. Three subject compounds, compounds A, B, and C, are presented in this embodiment. Two types of measurement conditions (events 1 and 2) different in the mass-to-charge ratio of the precursor ion are set for the compound A. One type of measurement condition (event 3) is set for the compound B, and one type of measurement condition (event 4) is also set for the compound C. During the measurement, the events 1 to 4 are repeatedly executed in sequence. The measurement conditions for a large number of compounds, including the compounds A, B, and C, are stored in the storage unit 41. An analyst reads and sets necessary conditions as and when necessary.

FIG. 3 illustrates a total ion chromatogram reflecting the retention time of each component contained in a sample. According to this chromatogram, the components in the sample elute at times t1, t2, and t3.

Figure 2:
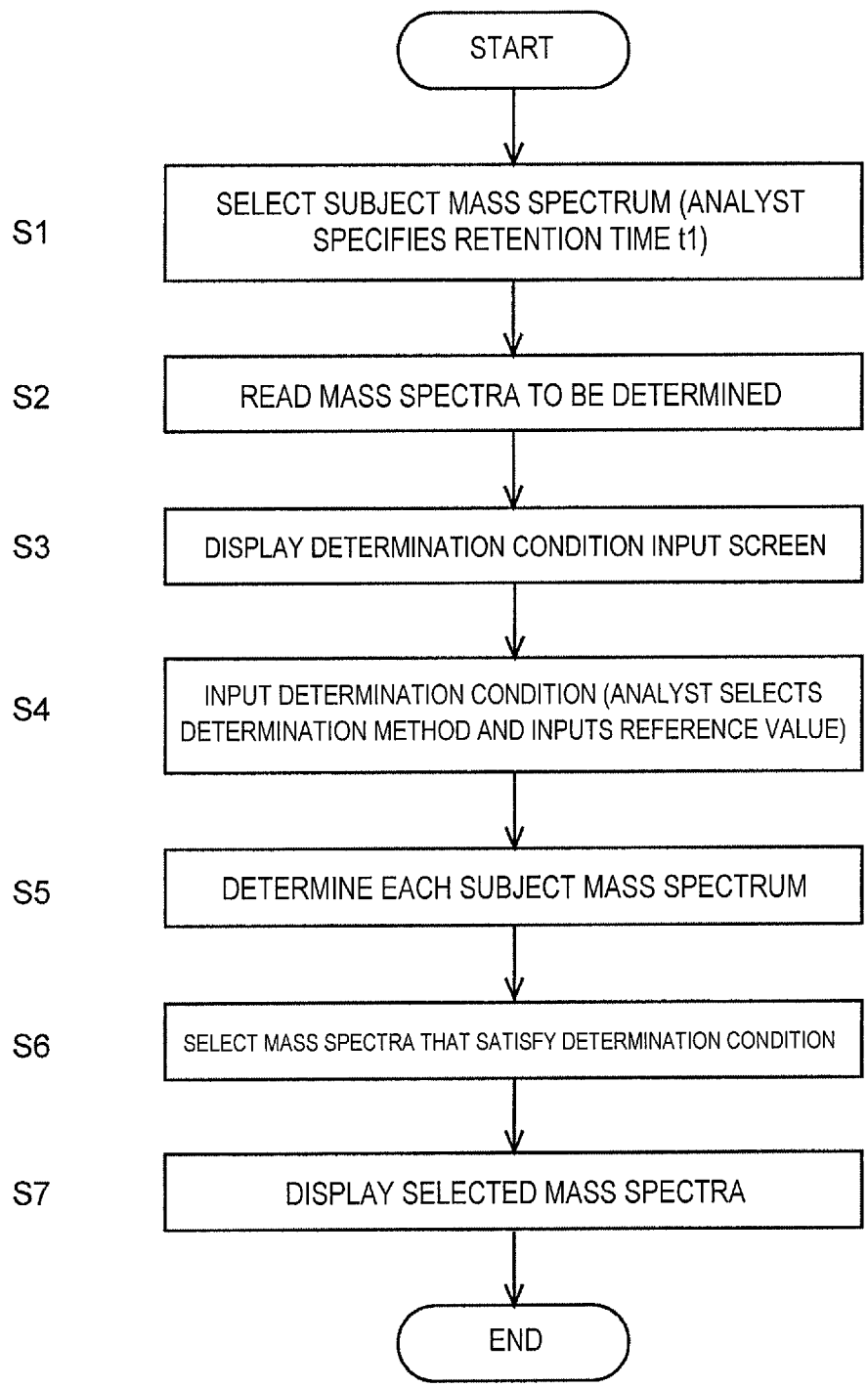
FIG. 2 is a flow chart illustrating one embodiment of the mass analysis data processing method according to the present invention.

FIG. 2 is a flow chart illustrating the flow of data processing in this embodiment.

When the analyst who confirmed the total ion chromatogram selects the time t1 at which a certain component was eluted (step S1), the data of mass spectra obtained by executing the events 1 to 4 at time t1 is read from the storage unit 41 (step S2). At the same time, the determination condition input unit 43 displays a determination condition input screen illustrated in FIG. 4 on the display 7 (step S3), and encourages the analyst to make an entry. The determination condition screen includes three types of determination methods including "intensity threshold", "effective intensity %", and "reference S/N ratio." The determination condition screen also includes check boxes for switching selection/non selection of these methods, and input boxes for inputting a determination reference value for each determination condition. An explanatory note concerning the determination method selected by the analyst is displayed on the lower portion of the screen. In the example illustrated in FIG. 4, "intensity threshold" is selected by the analyst, and therefore the explanatory note "mass spectra with maximum intensity at or under the threshold are not displayed" is displayed.

Once input of the determination condition (selection of determination method and input of determination reference value) by the analyst is completed (step S4), the determination execution unit 44 reads the data constituting the mass spectra each acquired when the events 1 to 4 were executed at time t1, and determines whether or not these four mass spectra satisfy the determination condition (step S5).

Figure 5:
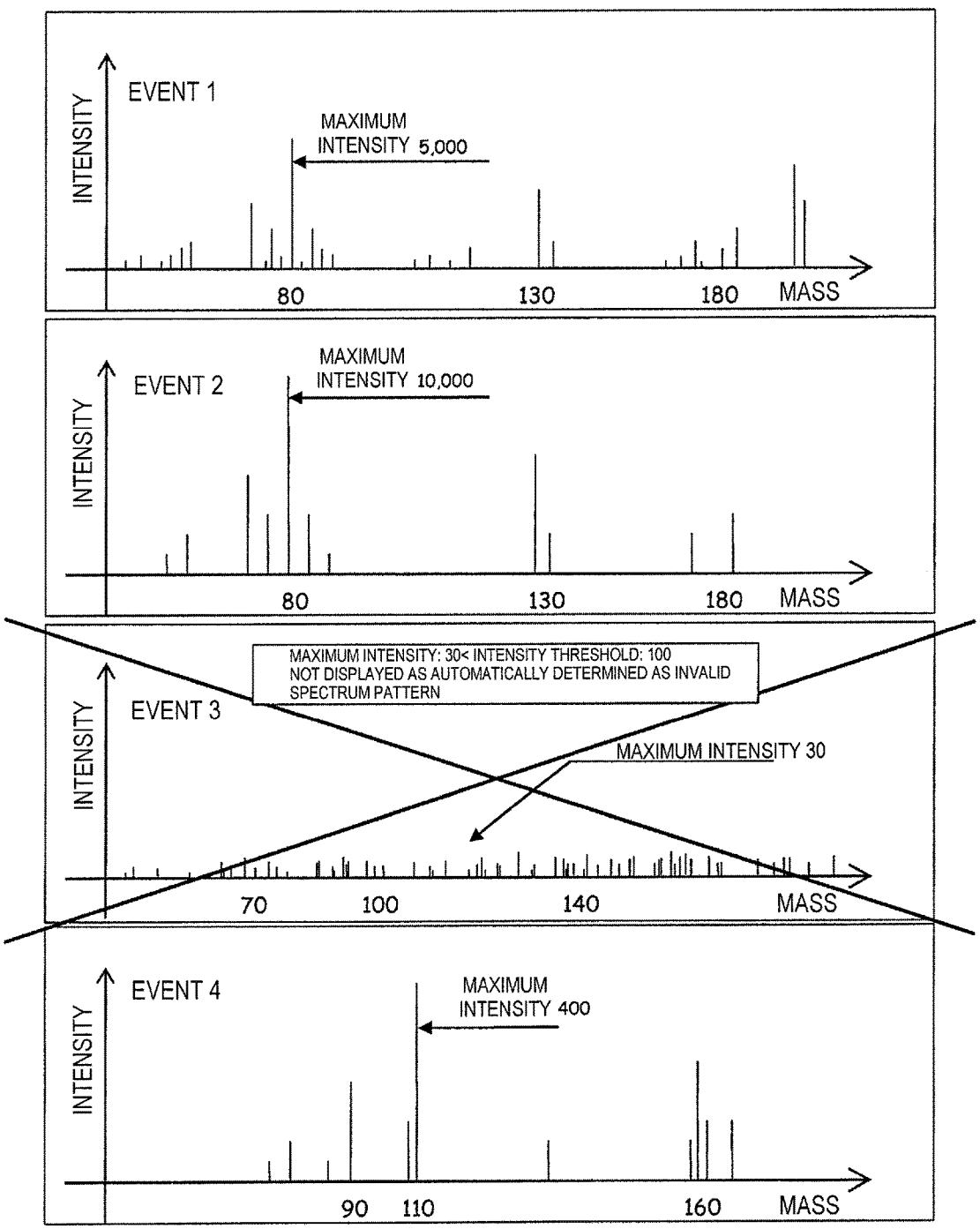
FIG. 5 is a mass analysis data processing result in this embodiment.

FIG. 5 illustrates the mass spectra acquired in the events 1 to 4. The maximum mass peak intensities in the mass spectra acquired in the events 1 to 4 are 5,000 (event 1), 10,000 (event 2), 30 (event 3), and 400 (event 4), respectively. As described before, since the intensity threshold as the determination condition is 100, the determination execution unit 44 determines that the mass spectra of the events 1, 2, and 4 satisfy the determination condition. Then, the selection result presentation unit 45 selects these three mass spectra, which were determined to satisfy the determination condition by the determination execution unit 44 (step S6), and displays the selected spectra on the display 7 (step S7).

Thus, when the mass analysis data processing apparatus and method of this embodiment are used, the analyst does not need to check the mass spectra on which only noises appear, as shown in the mass spectrum of the event 3. This makes it possible to reduce the burden on the analyst in checking the mass spectra. In this embodiment, three subject compounds and four events are set for easy understanding. However, in an actual inspection, several dozens of subject compounds are selected and at least one event is set for each of these compounds. When the number of the subject compounds are larger, about 100 mass spectra are acquired for one eluted component. If the apparatus and method of this embodiment are used, only the spectra effective for inspection and/or presumption of an unidentified component may be checked even when a large number of mass spectra are acquired. This makes it possible to considerably reduce the burden on the analyst.

A description is now given of the case where the analyst selects "effective intensity (%)" as a determination condition, and inputs 10 (%) as a determination reference value. The subject compounds, the events, and the mass spectra acquired when each event is executed are the same as those described before.

Figure 6:
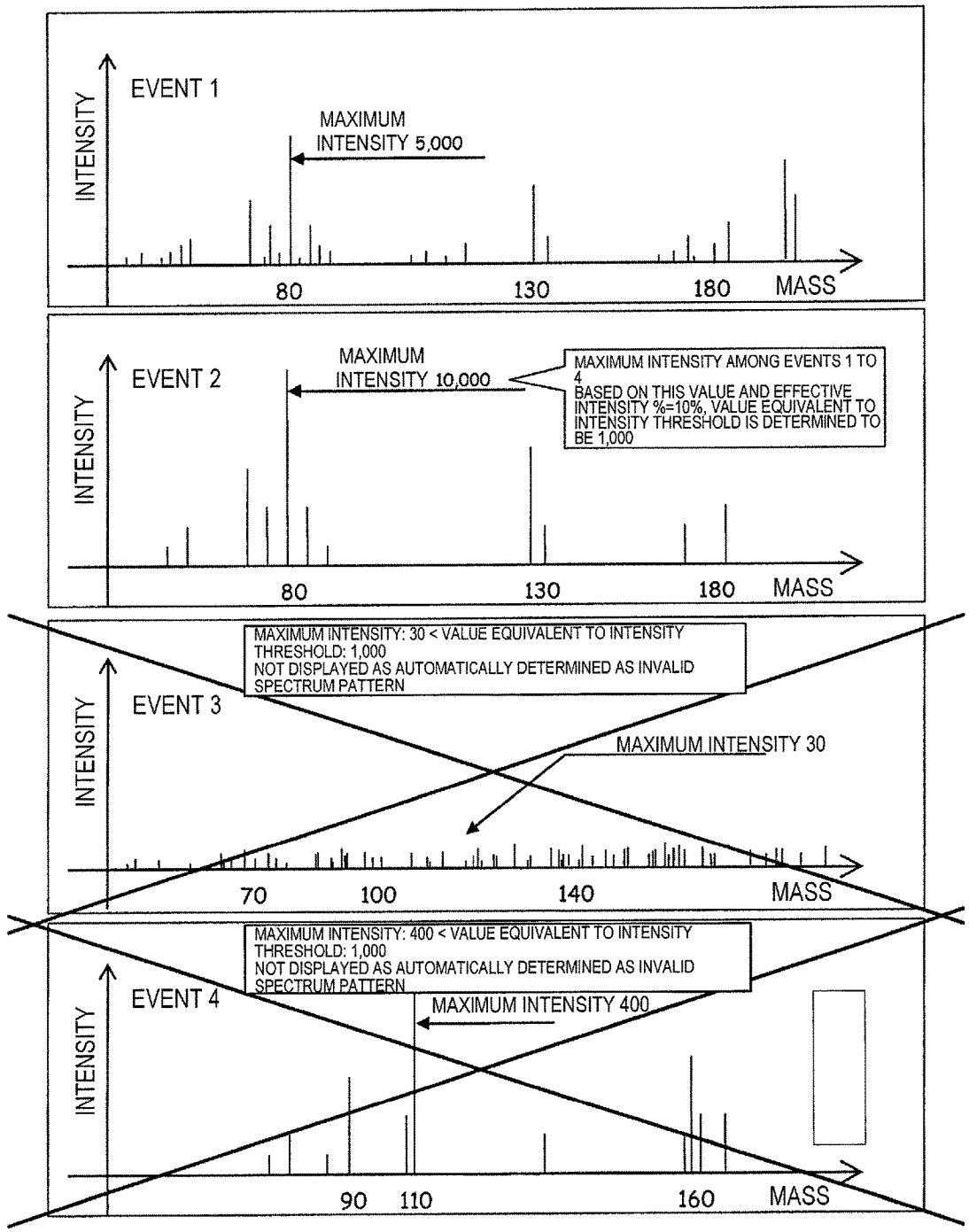
FIG. 6 is another mass analysis data processing result in this embodiment.

When the determination condition is "effective intensity (%)", the determination execution unit 44 first selects a maximum intensity from the mass peaks on all the mass spectra. In this case, the mass peak (intensity: 10,000) on the mass spectrum of the event 2 is selected. Then, 10% of this intensity, i.e., an intensity of 1,000, is set as a threshold, and the mass spectra containing the mass peaks exceeding this threshold are determined to satisfy the determination condition. In this example, the mass spectra of the events 1 and 2 are determined to satisfy the determination condition (see FIG. 6), and these mass spectra are displayed on the display 7 by the selection result presentation unit 45.

In this example, it is determined that the mass spectrum of the event 4, which was determined to satisfy the determination condition in the previously described example, does not satisfy the determination condition. The event 4 represents a measurement condition in which the ion characterizing the compound C is set as a precursor ion. In this embodiment, since the mass-to-charge ratio of a small amount of adduct ions generated from the compound A matches with the mass-to-charge ratio of the precursor ion set in the event 4, mass peaks appear on this mass spectrum. However, since the amount of generated adduct ions is generally smaller than the amount of generated univalent ions set as a precursor ion of the subject compound, the mass peak intensities attributed to the abduct ions are lower on the mass spectra. In the case of this embodiment, the compound A was eluted at time t1, and so the mass spectrum acquired under the measurement condition set for the compound C does not contribute to the presumption of an unidentified component. In this embodiment, the mass spectrum, on which a mass peak appears due to accidental matching of the mass-to-charge ratio of the precursor ion, is also excluded.

A description is now given of the case where the analyst selects "reference S/N ratio" as a determination condition, and inputs 30 as a determination reference value. The subject compounds, the events, and the mass spectra acquired when each event is executed are the same as those described before.

Figure 7:
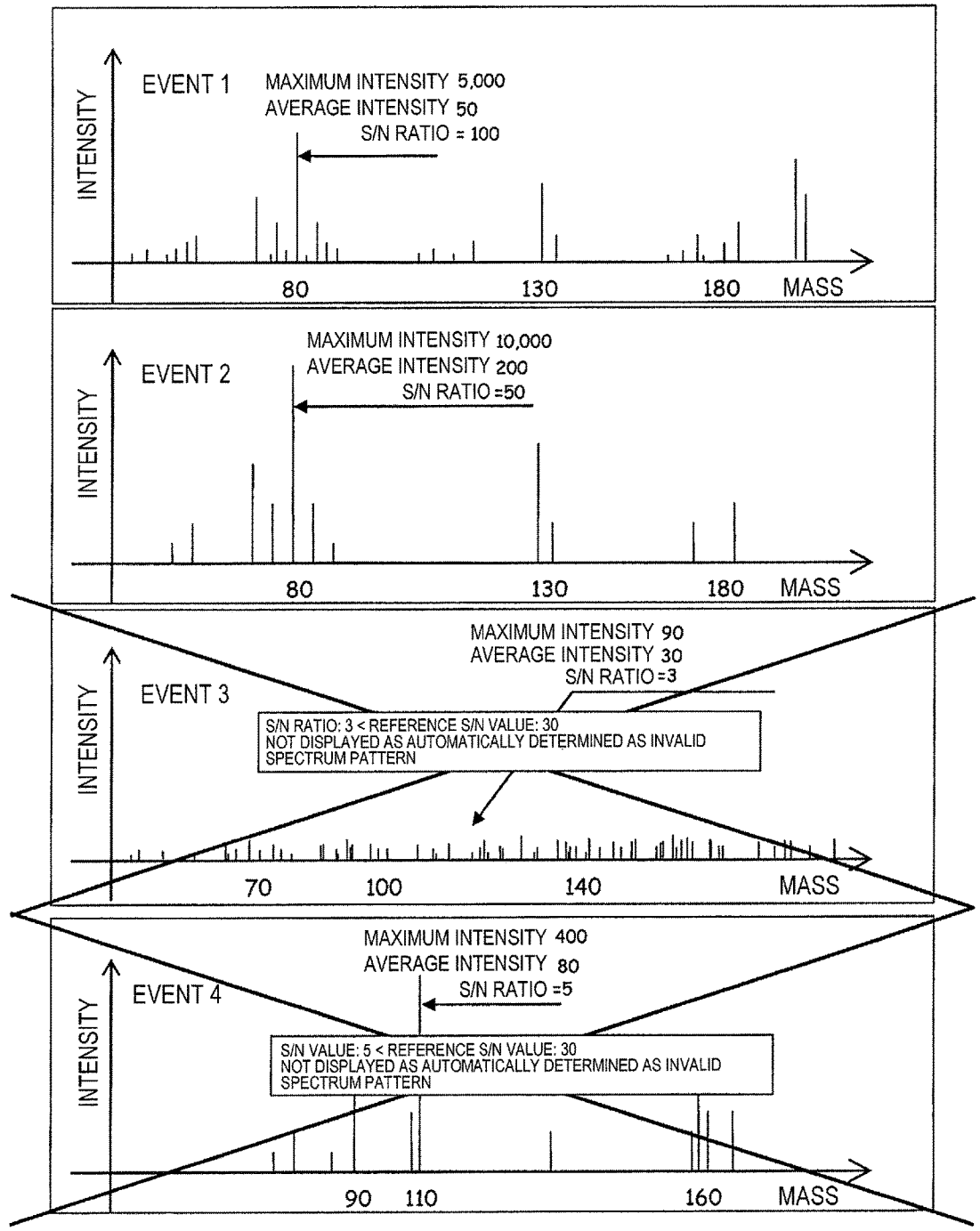
FIG. 7 is still another mass analysis data processing result in this embodiment.

When the determination condition is "reference S/N ratio", the determination execution unit 44 calculates a ratio between a maximum mass peak intensity and an average intensity of all the mass peaks in each of the mass spectra. Then, by using the ratio being 30 or more as a determination condition, the determination execution unit 44 determines whether or not each mass spectrum satisfies the condition. In this example, it is determined that the event 1 (value of ratio: 100) and the event 2 (value of ratio: 50) satisfy the determination condition, whereas the event 3 (value of ratio: 3) and the event 4 (value of ratio: 5) do not satisfy the determination condition (see FIG. 7). Based on this determination result, the selection result presentation unit 45 selects the mass spectra of the events 1 and 2, and displays them on the display 7.

Although one method is used as the determination condition in the above description, a plurality of determination conditions may be used in combination. In that case, the apparatus may be configured so that only the mass spectra that satisfy all the plurality of determination conditions set by the analyst are selected and presented to the analyst.

The above-disclosed embodiment is merely an example and may properly be changed within the meaning of the present invention.

In the above embodiment, the mass spectrum data acquired in the LC/MS/MS is processed. The same processing can similarly be applied in the case where one or more measurement conditions are set for a plurality of subject compounds, and mass spectra are individually acquired under each of the conditions. The mass spectra acquired by scan measurement (precursor ion scan measurement and neutral loss scan measurement) other than the product ion scan measurement may similarly be handled. In other words, the apparatus and method of this embodiment can be used to process the mass spectra acquired by performing $MS^n$ (n is an integer equal to or more than two) measurement.

Although the selection result presentation unit 45 is configured to display the mass spectra selected based on the determination result on the display 7 in this embodiment, the selected mass spectra may be presented to the analyst by such operation as outputting the result selected by the selection result output unit as data.

REFERENCE SIGNS LIST

1 ... Liquid Cromatograph Unit
10 ... Mobile Phase Container
11 ... Pump
12 ... Injector
13 ... Column
2 ... Mass Analyzing Unit
20 ... Ionization Chamber
201 ... ESI Probe
202 ... Heating Capillary
21 ... First Middle Vacuum Chamber
211 ... Ion Guide
212 ... Skimmer
22 ... Second Middle Vacuum Chamber
221 ... Ion Guide
23 ... Chemical Chamber
231 ... Front-stage Quadrupole Mass Filter
232 ... Collision Cell
233 ... Ion Guide
234 ... Rear-stage Quadrupole Mass Filter
235 ... Ion Detector
24 ... Power Supply Unit
4 ... Data Processing unit
41 ... Storage unit
42 ... Mass Spectrum Preparation Unit
43 ... Determination Condition Input Unit
44 ... Determination Execution Unit
45 ... Selection Result Presentation Unit

The invention claimed is:

1. A mass analysis system, comprising:
a mass analyzing unit that performs $MS^n$ (n is an integer equal to or more than two) measurement of an unidentified component contained in a sample under a plurality of different measurement conditions and obtains a plurality of $MS^n$ spectra each of which respectively corresponds to each of the plurality of different measurement conditions;
a display; and
a mass analysis data processing apparatus for processing data constituting the plurality of $MS^n$ spectra, the mass analysis data processing apparatus comprising:
a) a determination condition input unit for allowing an analyst to input a determination condition concerning a maximum intensity value of mass peaks on the $MS^n$ spectra obtained by the mass analyzing unit using an input unit, or for reading out an intensity value stored in a memory as the determination condition;
b) a determination execution unit for determining whether or not the determination condition is satisfied in each of the plurality of $MS^n$ spectra; and
c) a selection result presentation unit for selecting $MS^n$ spectrum or $MS^n$ spectra, determined to satisfy the determination condition by the determination execution unit, and presenting only the selected $MS^n$ spectrum or $MS^n$ spectra to the analyst on the display, and not presenting $MS^n$ spectrum or $MS^n$ spectra that does not satisfy the determination condition on the display.

2. The mass analysis data processing apparatus according to claim 1, wherein, the determination condition is that there is included a mass peak intensity exceeding a threshold value input by the analyst.

3. The mass analysis data processing apparatus according to claim 2, wherein,
the determination condition is that there is included a mass peak intensity equal to or more than a value obtained by multiplying a maximum intensity value, among each of mass peak intensities appearing on the plurality of mass $MS^n$, by a rate input by the analyst.

4. The mass analysis data processing apparatus according to claim 3, wherein
the determination condition is a ratio between an intensity value of a maximum intensity mass peak in each of the $MS^n$ spectra and an average value of all the mass peak intensities on each of the $MS^n$ spectra being equal to or more than a value input by the analyst.

5. The mass analysis data processing apparatus according to claim 2, wherein
the determination condition is a ratio between an intensity value of a maximum intensity mass peak in each of the mass spectra and an average value of all the mass peak intensities on each of the $MS^n$ spectra being equal to or more than a value input by the analyst.

6. The mass analysis data processing apparatus according to claim 1, wherein,
the determination condition is that there is included a mass peak intensity equal to or more than a value obtained by multiplying a maximum intensity value, among each of mass peak intensities appearing on the plurality of $MS^n$ spectra, by a rate input by the analyst.

7. The mass analysis data processing apparatus according to claim 6, wherein
the determination condition is a ratio between an intensity value of a maximum intensity mass peak in each of the $MS^n$ spectra and an average value of all the mass peak intensities on each of the $MS^n$ spectra being equal to or more than a value input by the analyst.

8. The mass analysis data processing apparatus according to claim 1, wherein
the determination condition is a ratio between an intensity value of a maximum intensity mass peak in each of the $MS^n$ spectra and an average value of all the mass peak intensities on each of the $MS^n$ spectra being equal to or more than a value input by the analyst.

9. The mass analysis data processing apparatus according to claim 1, wherein,
the determination condition is constituted of a plurality of combinations of the conditions including:
that there is included a mass peak intensity exceeding a threshold value input by the analyst; that there is included a mass peak intensity equal to or more than a value obtained by multiplying a maximum intensity value, among each of mass peak intensities appearing on the plurality of $MS^n$ spectra, by a rate input by the analyst; and a ratio between an intensity value of a maximum intensity mass peak in each of the $MS^n$ spectra and an average value of all the mass peak intensities on each of the $MS^n$ spectra being equal to or more than a value input by the analyst.

10. A mass analysis method for processing data constituting a plurality of $MS^n$ spectra acquired by performing $MS^n$ (n is an integer equal to or more than two) measurement of an unidentified component contained in a sample under a plurality of different measurement conditions by a mass analyzer and obtaining a plurality of $MS^n$ spectra each of which respectively corresponds to each of the plurality of different measurement conditions, the method comprising:
a) allowing an analyst to input a determination condition concerning a maximum intensity value of mass peaks on the MS$^n$ spectra using an input unit or for reading out an intensity value stored in a memory as the determination condition;
b) determining whether or not the determination condition is satisfied in each of the plurality of MS$^n$ spectra; and
c) selecting a MS$^n$ spectrum or mass spectra, determined to satisfy the determination condition, and presenting the MS$^n$ spectrum or spectra to the analyst on a display, and not presenting MS$^n$ spectrum or MS$^n$ spectra that does not satisfy the determination condition on the display.

* * * * *